United States Patent
Gargus et al.

(10) Patent No.: US 6,183,975 B1
(45) Date of Patent: Feb. 6, 2001

(54) METHOD OF DETECTION OF CONGENITAL DISEASE

(76) Inventors: J. Jay Gargus, 34 Urey Ct., Irvine, CA (US) 92612; Mark Estacion, 25709 Peppercorn Dr., Westlake, OH (US) 44145

(*) Notice: Under 35 U.S.C. 154(b), the term of this patent shall be extended for 0 days.

(21) Appl. No.: 09/030,580

(22) Filed: Feb. 24, 1998

Related U.S. Application Data (60) Provisional application No. 60/038,802, filed on Feb. 24, 1997.

(51) Int. Cl.[7] ............................ C12Q 1/02; G01N 33/567
(52) U.S. Cl. ..................... 435/7.21; 435/29; 436/63; 436/79; 436/503; 436/510; 436/906
(58) Field of Search ...................... 435/7.21, 29; 436/63, 436/79, 503, 510, 906

(56) References Cited

U.S. PATENT DOCUMENTS 5,501,961 * 3/1996 McMurchie et al. ................. 436/503
5,580,748 * 12/1996 Alkon et al. ........................... 435/29

OTHER PUBLICATIONS

Munaron et al, Journal of Physiology, 484, (3), 557–566, 1995.*

\* cited by examiner

*Primary Examiner*—David Saunders
(74) *Attorney, Agent, or Firm*—Gray Cary Ware & Freidenrich LLP; Lisa A. Haile, Ph.D.

(57) ABSTRACT

A method for diagnosing a congenital disease by determining a cell's response to activation of a membrane receptor using a physiological indicator is provided. The method of the invention uses fetal or adult cells in a non-invasive screen for congenital disorders.

32 Claims, 7 Drawing Sheets

FGF-INDUCED CALCIUM SIGNALING

METHOD OF DETECTION OF CONGENITAL DISEASE

CROSS REFERENCE TO RELATED APPLICATIONS

This application claims priority from U.S. Provisional Application Serial No. 60/038,802 filed Feb. 24, 1997.

FIELD OF THE INVENTION

The present invention relates generally to the field of genetic testing and more specifically to a method for diagnosing a congenital disease by determining a cell's response to activation of a membrane receptor using a physiological indicator.

BACKGROUND

Genetic testing has been increasingly utilized during prenatal care. Beginning at approximately nine weeks of gestation, the health and genetic status of the fetus can be examined by a variety of prenatal diagnostic techniques. Two approaches, ultrasonography and the measurement of α-fetoprotein in maternal serum, are increasingly being used for diagnosis in the absence of other indications. Ultrasonography allows determination of gestational age, identification of grossly abnormal development, identification of major developmental abnormalities of the head, spine, head, gastrointestinal tract, kidney and skeleton, and detection of multiple gestations (Diagnostic Ultrasound: Applied to Obstetrics and Gynecology, 2nd Ed., Sabbagha, R. E. (ed.), J. B. Lippincott Co., Philadelphia, 1987, p.2). The maternal serum α-fetoprotein level is used to screen pregnancies for several disorders: Elevated values raise the possibility of a fetal neural tube defect and low levels raise the possibility of trisomy 21, or, less frequently, trisomy 18. In either case, further tests are often required to confirm that abnormal α-fetoprotein level is the result of a congenital disorder rather than a false positive result.

Chorionic villus sampling and amniocentesis are both methods which are used to provide a sample of fetal cell for cytogenetic and, when indicated, metabolic or molecular analyses. Analysis of fetal cells currently allows for the prenatal diagnosis of more than 200 Mendelian disorders, most of the major chromosomal disorders, and some multifactorial disorders. In chorionic villus sampling, a biopsy of mixed fetal and maternal cells is obtained from the chorion frondosum using a transcervical or transabdominal approach. The fetal cells are then mechanically separated for analyses. Amniocentesis relies on procuring a sample of amniotic fluid from the pregnant woman, which is then separated into the cellular component (used for cytogenetic, biochemical, and molecular analyses) and the fluid supernatant (used to measure the α-fetoprotein concentration). Cytogenetic karyotype analysis on cells obtained through either procedure is a routine recommended screen in all pregnancies to mothers age 35 or older and is now a major biomedical industry. Other tests on cells obtained through these procedures are performed much more rarely, and only when specifically indicated, not as a screening procedure. Fetal cells can also be obtained by cordocentesis, or percutaneous umbilical blood sampling, although this technique is technically difficult and not widely available (see Erbe, R. W., 1994, in: Scientific American Medicine, Volume 2, section 9, chapter IV, Scientific American Press, New York, pp 41–42). In the majority of cases prenatal diagnostic studies are a routine component of standard medical care in individuals with no specific risks other than age.

However, in many instances, individuals or couples seek genetic information because a relative has a genetic disorder or condition known to have a genetic component. The reproductive alternatives available to a couple or individual at risk depend on the specific disorder and the availability of tests for the disorder.

Mutations in the fibroblast growth factor receptor (FGFR) gene family (designated FGFR1, PGFR2, and FGFR3) have recently been shown to underlie several dominantly inherited disorders of bone development. FGFR1 mutations have been shown to produce Pfeiffer syndrome, FGFR2 mutations have been shown to produce Crouzon, Jackson-Weiss, Pfeiffer and Apert syndromes, and FGFR3 mutations have been shown to cause achondroplasia, thanatophoric dysplasia types 1 and 2, hypochondroplasia, and Crouzon syndrome with acanthosis nigricans and FGFR3-associated coronal synostosis (reviewed in Wilkie, A. O. M., et al., 1995, Current Biol. 5:500–507; Mulvihill, J. J., 1995, Nature Genet. 9:101–103). All of the mutant disease-causing alleles found in the three receptor types are dominant. And most appear sporatically as a result of new mutations, not in families at known risk for the disease. Mutations at different FGFR loci can give the same disease phenotype and a given allele can produce different disease phenotypes. The majority of the different alleles appear to alter a common structure, the receptor dimer. This suggests that mutations in all three types of FGFR may share a common pathophysiological mechanism. However, no defect in receptor function has previously been directly demonstrated for these mutations.

Previous studies have used conventional knockout mice (e.g., Colvin, J. S., et al., 1996, Nature Genet. 12:390–397) or in vitro studies of transfected chimeric receptors (e.g., Webster, M. K., and Donoghue, D. J., 1996, EMBO J. 15:520–527; Galvin, B. D., et al., 1996, Proc. Natl. Acad. Sci. U.S.A. 93:7894–7899) to examine FGF receptors. However, these studies do not fully mimic the native or disease state.

Most tissues express multiple FGFR types, including splice variants of each, and most FGF ligands discriminate poorly between the receptor types. Both hetero- and homo-receptor dimers contribute to signaling (Johnson, D. E., and Williams, L. T., 1993, J. Biol. Chem. 267:1470–1476). Model negative dominant mutations in one receptor class can create a dosage-dependent inhibition of all FGF signaling, even though many wild-type FGF receptors of the same and different type are expressed. This kind of interaction between the FGFR types has been defined in transfected cultured cells, injected Xenopus oocytes, embryos, and the epidermis of transgenic mice.

SUMMARY OF THE INVENTION

In a first embodiment the invention provides a method for detecting a congenital disorder resulting from an altered membrane component by providing a sample of fetal cells; contacting the cells with a substance normally able to activate the membrane component in a wild type cell; and determining an intracellular second messenger response. For example, the membrane component is a receptor such as FGF receptor.

In another embodiment, the invention provides a method of detecting a congenital disorder by providing a sample of pre-natal cells; introducing a physiological indicator into the cell; contacting the cells with a ligand; detecting the effect of the ligand on the physiological indicator in the sample of pre-natal cells; and comparing the effect of the ligand on the physiological indicator with the effect of the ligand on the physiological indicator in a control cell.

In yet another embodiment the invention provides a method of detecting a genetic disorder resulting from an altered membrane component. The method includes providing a sample of cell; contacting the cells with a substance normally able to activate the membrane component in a wild type cell; and determining an intracellular second messenger response. The method of the invention are also useful for detecting such disorders postnatally.

DESCRIPTION OF THE DRAWINGS

FIG. 1 shows examples of intracellular calcium responses to 50 ng/ml bFGF in wild-type human fibroblasts over a 20 min period. $G_0$-arrested cells were loaded with fura-PE3 and then measured and analyzed using a digital video image processor. Each plot corresponds to a region over a single cell and the cells chosen are meant to illustrate the kinds and relative proportions of signaling phenotypes. The Y-axes report the signal fluorescence ratio, which can be transformed into a free calcium concentration through standard calibration methods. In the system used, a fluorescence ratio of 0.5 corresponds to a calibrated calcium level of 130 nM. The X-axes are in units of seconds. During baseline recording, cells maintained a stable resting level of intracellular calcium between 100 and 200 nM. Within a few minutes of bFGF stimulation (first arrow), cells asynchronously respond with a rise in intracellular calcium, establishing a signal of characteristic morphology.

FIG. 2 shows that calcium signals induced by bFGF in fibroblasts are dependent upon extracellular calcium. Wild-type fibroblasts were loaded with dye, measured, and analyzed.

FIGS. 3A and 3B show that calcium signaling by fibroblasts in response to bFGF is altered by mutations in FGFR3. FIGS. 3A, 3B, 3C, and 3D each show eight representative cells from genotyped individuals having homozygous achondroplasia, heterozygous achondroplasia, heterozygous TD1 thanatophoric dysplasia, or heterozygous TD2 thanatophoric dysplasia, respectively. To allow for a condensed presentation, the tracings are offset vertically from each other and the Y-axis tick-marks represent 0.5 fluorescence ratio units. A homozygous G380R mutation in FGFR3 eliminates calcium signaling by all FGF receptors and effectively abolishes the composite response to bFGF (FIG. 3A); however, the heterozygous G380R genotype gives a normal calcium signal (FIG. 3B). A single TD1 mutant allele of FGFR3 results in the complete inhibition of all bFGF-dependent calcium signaling (FIG. 3C), whereas a single K650E TD2 allele of FGFR3 does not alter calcium signaling (FIG. 3D). Note that none of the above mutations has any effect on the baseline calcium or on the ability of bradykinin to elicit a control calcium signal. Statistical analysis of the prestimulation ratio values by ANOVA showed no significant differences between any groups or between any group and wild-type.

FIG. 4 shows a model for FGF receptor signaling. FGF binds to heparin and produces hetero- and homo-multimers of the FGFRs, activating their endogenous tyrosine kinase. Within this complex the receptors undergo autophosphorylation on tyrosine residues. PL$\gamma$ docks on phosphotyrosine 766, becomes phosphorylated and active, cleaving phosphatidylinositol 4,5-bisphosphate (PIP2) to diacylglycerol (DAG) and inositol 1,4,5-triphosphate (IP3). DAG activates Protein kinase C (PKC) and IP3 releases calcium from intracellular stores by binding to an IP3 receptor. The mechanism by which the calcium conducting ion channel in the plasma membrane becomes activated remains to be determined, but the majority are not Icrac channels.

DESCRIPTION OF THE PREFERRED EMBODIMENTS

The present invention provides a method for detecting a congenital disorder in a subject. A "congenital disorder" is a disorder existing at, and usually before, birth, regardless of its causation. Congenital disorders can be the result of a genetic change (e.g., a mutation or deletion of a gene), the result of infection (e.g., syphilis), the result of nutrition (e.g., a vitamin deficiency), or the result of exposure to an exogenous agent or toxin (e.g., thalidomide or an environmental toxicant), for example. Preferably the subject is a human.

Screening methods are used to test for classes of disease when there are no specific indications this disease might exist. The screening methods of the invention are useful for detection of disorders, such as congenital disorders, that result from an altered membrane component. Membrane components include, but are not limited to polypeptide and phospholipid components. Examples of polypeptide membrane components are receptors, channel proteins, enzymes, and structural proteins. A "receptor polypeptide" is a polypeptide found on a cell, often on a membrane, that can combine with a specific type of molecule to alter a function of the cell. Examples of receptor polypeptides include, but are not limited to, growth factor receptors, hormone receptors, cytokine receptors, ligand-gated channels and steroid receptors. Examples of receptors of are listed in Table I.

TABLE I

Receptors

| Gene Product | Genbank Accession No. |
|---|---|
| Human insulin receptor gene | M29929 |
| Human somatostatin receptor gene | L14856 |
| Human IL-2 receptor gene | X01057, X01058, XD1402 |
| Human TGF receptor (mRNA) | M8509 |
| Human PDGF receptor (mRNA) | M22734 |
| Human EGF receptor gene | X06370 |
| Human NGF receptor (mRNA) | M14764 |
| Human FGF receptor (mRNA) | M34641 |
| Human GM-CSF receptor (mRNA) | M73832 |
| Human IFN-γ receptor (mRNA) | X62468 |

A "channel polypeptide" is a polypeptide embedded in the cell membrane which is part of a structure that determines what particle sizes and or charges are allowed to diffuse into the cell. Channel polypeptides include the "ion channels", which are proteins imbedded in a cell membrane that serve as a crossing point for the regulated transfer of a specific ion or group of ions across the membrane. Examples of channel polypeptides include, but are not limited to, the voltage insensitive channels including the potassium, sodium, and calcium channels, and the voltage sensitive channels including the potassium, sodium, and calcium channels. Several ion channel polypeptides are listed in Table II.

TABLE II

Ion Channels

| Gene Product | Genbank Accession No. |
|---|---|
| Human voltage-gated chloride ion channel CLCN5 | X91906 |
| Human delayed rectifier potassium channel (Isk) gene | L33815 |
| Human potassium channel protein (HPCN3) gene | M55515 |
| Human potassium channel (HPCN2) (mRNA) | M55514 |
| Human potassium channel (HPCN1) (mRNA) | M55513 |
| Human gamma subunit of epithelial amiloride-sensitive sodium channel (mRNA) | X87160 |
| Human beta subunit of epithelial amiloride-sensitive sodium channel | X87159 |

An "enzyme" is a polypeptide that acts as a catalyst, which speeds the rate at which biochemical reactions proceed but do not alter the direction or nature of the reaction. Examples of enzyme polypeptides include, but are not limited to, protein kinases, catalyses, amidases and phosphorylases. Several examples are listed in Table 3.

In one embodiment of the invention, a sample of fetal cells is provided. The fetal cells may be obtained by methods known to one of skill in the art. For example, amniocentesis, chorionic villus sampling (CVS), percutaneous umbilical blood sampling (PUBS), or fetal biopsy may be used to obtain fetal cells or fetal tissue containing fetal cells.

A cell sample can also be obtained postnatally if desired. By "postnatal" is meant any time after birth. A cell sample can be obtained by methods known in the art, for example, by biopsy or needle aspiration. A cell sample can be obtained from any tissue of interest. In a preferred embodiment, the sample of cells is a skin biopsy or sample of blood.

TABLE III

Enzymes

| Gene Product | Genbank Accession No. |
|---|---|
| Human cAMP dependent protein kinase AKAD 79 (mRNA) | M90359 |
| Human protein kinase C beta gene | D10022 |
| Human lipid-activate protein kinase PRK-1 (mRNA) | U33053 |
| Human guanine nucleotide binding protein alpha subunit gene | M21142, J03647, M21139 |
| Human serine/threonine kinase (mRNA) | M83780 |

The method of the invention includes contacting the cells with a substance that is able to activate a particular membrane component in a wild type cell. By "wild type cells" is meant cells having a normal second messenger response upon activation of the membrane component. Examples of "wild type cells" are cells from an established cell line, cells isolated from an unaffected fetus (i.e, not having a congenital disorder), or cells from the same fetus from tissue unaffected by the congenital disorder. In a preferred embodiment, the wild-type cells are from a cell line.

In one aspect, when the membrane component is a receptor, the ligand for the receptor is used to contact the cell. The ligand can be the natural ligand for the receptor, or can be a synthetic ligand produced by methods known in the art. In another aspect, when the membrane component is a channel, an ion that flows though the channel in a wild type cell is contacted with the fetal cells. In another aspect, when the membrane component is an enzyme, a substrate for the enzyme is contacted with the cell in such a way as to allow the enzyme and substrate to interact.

A "second messenger response" or "cell signaling event" as used herein refers to the generation of a biochemical or physiological response as a result of contacting a substance (e.g., an ion, a ligand, or a substrate) with the fetal cells. In general, a second messenger response results in the change of a molecular characteristic or parameter of the cell. Non-limiting examples of second messengers include ions, enzymes (e.g., serine/threonine kinases), cyclic nucleotides (e.g., cAMP, cADP, cGMP, cGDP), and the like. A specific, non-limiting, example of a second messenger response is the generation of a $Ca^{2+}$ flux following the interaction of the fibroblast growth factor receptor with fibroblast growth factor.

The second messenger response may be measured by any means known to one of skill in the art. In one embodiment, a "physiological indicator" is used to measure the second messenger response. A "physiological indicator" is any compound in which a measurable property changes in a response to a physical parameter of the cell. Cell signaling events that occur in vivo can be of very short duration. The physiological indicators used in the methods of the invention allow measurement of the physiological parameter, over the same time period that the event actually occurs. Alternatively, the physiological indicators allow measurement of a response after the event occurs (over a longer time period). One non-limiting example of a measurable property is a change is fluorescence of the indicator.

Fluorescence is one spectral property of which can be used as the means of detecting a physiological parameter of a cell. As used herein, the term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between an activated and an inactivated cell is sufficient for the utility of the fluorescent physiological indicator in a method of the invention. A measurable difference can be determined by determining the amount of any quantitative fluorescent property, e.g., the amount of fluorescence at a particular wavelength, or the integral of fluorescence over the emission spectrum. Optimally, the physiological indicator is selected to have fluorescent properties that are easily distinguishable.

A second non-limiting example of a means for detecting a response is a change in the physical location of the indicator. Movement of the indicator can be measured by means well known to one of skill in the art. For example, fluorescence activated cell sorting can be used to identify exclusion or uptake of a physiological indicator.

In a preferred embodiment, a physical parameter such as an ion flux, e.g. a calcium flux is detected. Many neuroendocrine, cytokine, and growth factor receptors produce cytosolic calcium waves in cultured cells. In the case of a calcium indicator flux, a calcium indicator dye is used as a physiological indicator. A calcium indicator dye is any compound which changes a physical parameter (e.g., fluorescence), in response to calcium ions. An example of a calcium indicator dye is fura-PE3.

In one embodiment, a calcium-indicator fluorescent dye is used to measure intracellular calcium signaling in living cells (see Tsien, R. Y., 1992, Am. J. Physiol. 263:C723–728). Uncharged esterified precursor dye passively equilibrates across the cell membrane, loading into intact cells due to intracellular esterase activity that releases charged unesterified active dye, trapping it in the cytoplasmic compartment. All cells of every shape and size are simultaneously loaded without needing microinjection or membrane damage. Furthermore, a dye's spectral properties allow for the calibrated conversion of dye signal into an intracellular calcium concentration while compensating for differences in cell thickness or dye photo bleaching. This is accomplished by determining a ratio of the dye signal recorded at two different wavelengths (see Examples).

Techniques for measuring calcium indicator dyes are well known in the art, such as single-cell ratiometric calcium image analysis (Estacion, M., et al., 1996, Am. J. Physiol. 270:C1145–1152). In this method, cells are loaded with calcium indicator (e.g., fura-PE3) in media containing fura-PE3. Light from a xenon arc lamp is passed though a motorized filter wheel containing 340- and 380-nm filters into an inverted microscope and the dye epifluorescence captured by a SIT camera. The signal is then processed by a video imaging system that performs background-subtracting and duel wavelength image ratioing. This ratio is a calibrated function of ionized calcium concentration.

High sensitivity video cameras and rapid image processors allow a ratiometric operation to be performed for each pixel element of a video image of a field of cells. Thus multiple single cells or even subcellular regions of cells in the field or view can be simultaneously visualized, analyzed and measured. A rapid repetitive resampling of a given field over time reconstructs the intracellular calcium signal from each element in the field as it responds to extracellular stimuli (Tsien, R. Y., 1992, supra).

Once the intracellular second messenger response is determined in the sample of fetal cells, this second messenger response can be compared to the second messenger response observed in a sample of wild-type cells.

A method of the invention can be used to detect genetic disorders resulting from alterations in a membrane component. A "genetic disorder" is a disorder resulting from a genetic change, such as a mutation in a specific gene. Examples of mutations are insertions, deletions, point mutations or frame shift mutations. The genetic change can occur in the gene encoding the membrane component itself, or can be in a gene which affects expression of the membrane component.

In one preferred embodiment, the invention can be used to detect the nature of the fibroblast growth factor receptor FGFR in fetal cells. Mutations in the fibroblast growth factor receptor (FGFR) gene family (designated FGFR1, FGFR2, and FGFR3) have recently been shown to underlie several dominantly inherited disorders of bone development such as Pfeiffer syndrome (FGFR1 mutations), Crouzon, Jackson-Weiss, Pfeiffer and Apert syndromes (FGFR2 mutations), and achondroplasia, thanatophoric dysplasia types 1 and 2, hypochondroplasia, Crouzon syndrome with acanthosis nigricans and FGFR3-associated coronal synostosis (FGFR3 mutations).

Four types of FGFR are known in the art: FGFR1, FGFR2, FGFR3, and FGFR4. Since, to date, attempts to define the pathogenesis of FGFR diseases have been limited to an analysis of either null alleles in vivo or expression of only the targeted mutant receptor in vitro, there has not yet been the potential to observe physiological signaling interactions between the host of FGF receptors.

The method of the invention can be used to detect a congenital disorder associated with an FGFR by identifying alterations in FGF receptors,(FGFR1, FGFR2, FGFR3, or FGFR4), or a combination thereof. The method of the invention can be used to examine FGF-induced signals, such as FGF-induced intracellular calcium signals, to identify pathological conditions associated with a mutation in a nucleic acid encoding a FGFR. A mutation in the nucleic acid encoding an FGFR includes any alteration such as an insertion, deletion, base pair mutation or frame shift in the nucleic acid which results in the production of an FGFR which differs from the wild-type FGFR. The method of the invention can also be used to examine mutations in nucleic acid encoding genes which interact with an FGFR, such that the expression or function of an FGFR is altered.

In an illustrative aspect of the invention, a sample of fetal cells either from a subject undergoing routine karyotype analysis or from a subject at risk for a specific a congenital disorder (e.g., due to an altered FGFR) or a subject suspected of having a congenital disorder is provided. A physiological indicator (e.g., fura-PE3) is introduced into the cells and the cells are then contacted with a ligand for the FGFR (e.g., bFGF). The ability of the ligand (bFGF) to induce a calcium signal is then examined using the physiological indicator. The calcium signal in the sample cells is then compared to the calcium signal in wild type cells having a normal second messenger response. If the calcium signal is the similar to the wild type cells, then the FGFR in the cell sample is unaltered. However, if the calcium signal differs substantially from the wild type cells, then the FGFR is an altered.

It is to be understood that this invention is not limited to the particular methodology, protocols, sequences, models and reagents described as such may, of course, vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, physiological indicators, and methodologies which are described in the publications which might be used in connection with the presently described invention.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLE 1

Materials and Methods

Cell Culture

Genotyped human fibroblast cell cultures were generously provided by Dr. J. J. Wasmuth (UC Irvine). Cells were maintained in tissue culture flasks in Dulbecco's minimum essential medium (DMEM) containing 10% fetal bovine serum at 37° C. in an atmosphere of 95% air and 5% $CO_2$. For each experiment, cells were plated at low density in the same growth medium on custom-made glass coverslip chambers. After 4–5 days of exponential growth, cells were $G_0$-arrested by culturing in serum-free DMEM medium for the final 24 hr preceding imaging.

Intracellular Calcium Measurements

The cells were loaded with calcium indicator dye by performing a 1 hour incubation at 37° C. in serum-free DMEM containing 4 $\mu$M fura-PE3 (Teflabs). After loading, the cells were washed and maintained in standard extracellular Ringer solution composed of (in mM) 160 NaCl, 4 KCl, 2.0 $CaCl_2$, 1 $MgCl_2$, 5 HEPES, and 10 glucose, adjusted to pH 7.2. For ratiometric imaging of intracellular calcium, light from a 75-W xenon arc lamp was passed through a motorized filter wheel containing 340- and 380-nm filters and a field of the dye-loaded cells imaged using a Zeiss IM 35 inverted microscope. Dye fluorescence is captured by a Hamamatsu C2400 SIT camera, and the signal is processed by a video imaging system (ETM Systems). Eight-bit images, averaged over 8 frames, were recorded every 8 sec for each wavelength. The raw images were first background subtracted and the resulting images were divided to obtain ratios of the fluorescence at 340 nm/380 nm. Regions of the image were defined to correspond to individual cells and the intracellular calcium (the fluorescence ratio) within each defined region was followed during the course of the experiment. Depending upon the density of the cells in a culture, between ten and fifty cells could be distinguished simultaneously in the imaged field of view. This generates a matrix of intracellular calcium measurements, reported as fluorescence ratios, for each region (cell) versus time. These values are transferred to a spreadsheet program (Sigmaplot) for analysis and figure generation. For dye calibration, the minimal fluorescence ratio, $R_{min}$, was measured using 1 $\mu$M ionomycin in Ringer solution buffered to 10 nM $CaCl_2$ (0.1 mM calcium, 11 mM EGTA) and the maximal fluorescence ratio, $R_{max}$, was similarly measured with Ringer solution supplemented to 10 mM $CaCl_2$. Conversion of the fluorescence ratio to a $Ca^{2+}$ concentration was performed according to Grynkiewicz et al. (Grynkiewicz, G., et al., 1985, J. Biol. Chem. 260:3440–3450).

All experiments were performed at room temperature. The solution in the chamber could be replaced using a perfusion system that takes approximately 15 seconds for a fivefold volume exchange. The bFGF (R & D Systems), Bradykinin (Calbiochem) and ATP (Sigma) were solubilized in water as 1000× stocks and stored as single-use aliquots at −30° C. These reagents were diluted into Ringer solution at their final concentrations on the day of experiment.

Statistics

Basic statistical analysis of means and standard deviations were calculated using either Excel or Sigmastat. Comparisons of datasets by ANOVA were performed using Sigmastat.

EXAMPLE 2 b-FGF Induced Calcium Signals in Wild-Type Human Diploid Fibroblasts

Figure 1A:
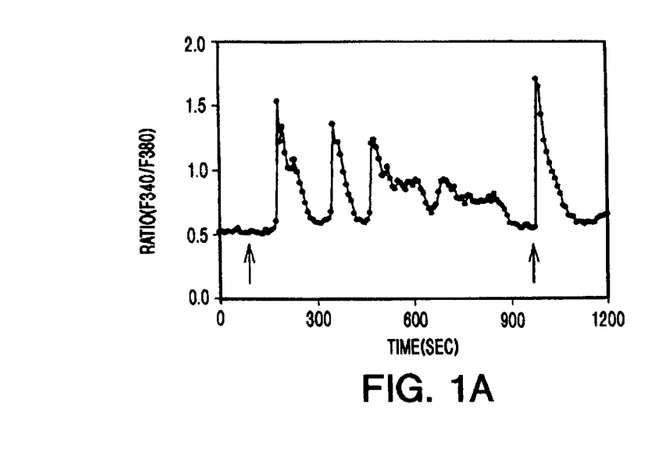
FIGS. 1A, 1B, and 1E show cells responding with an oscillating calcium signal, each peak and interpeak interval lasting approximately 2 min.
Figure 1B:
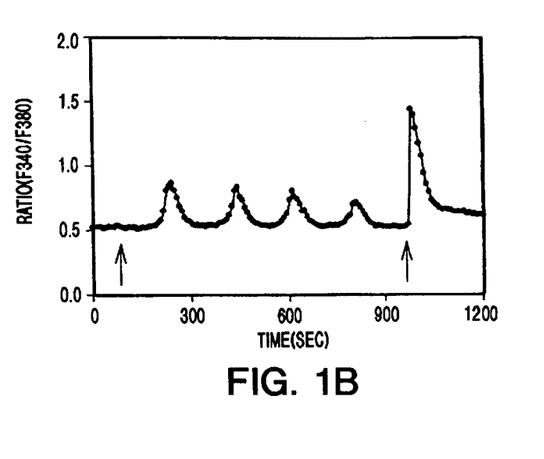
Figure 1C:
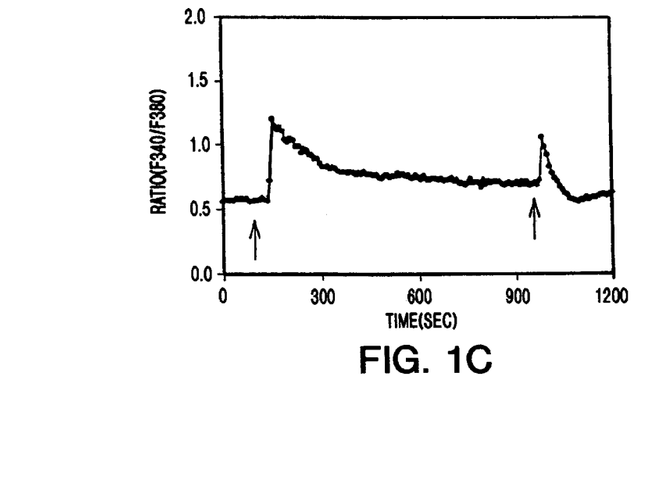
FIG. 1C shows a cell with a single prolonged plateau signal.
Figure 1D:
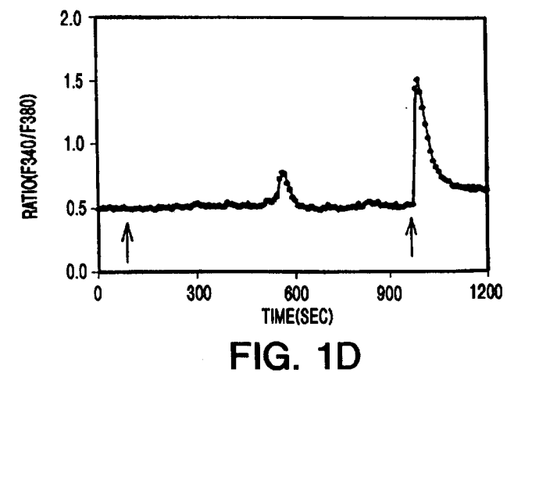
FIG. 1D shows one cell responding with a transient change in calcium lasting for about 1 min.
Figure 1E:
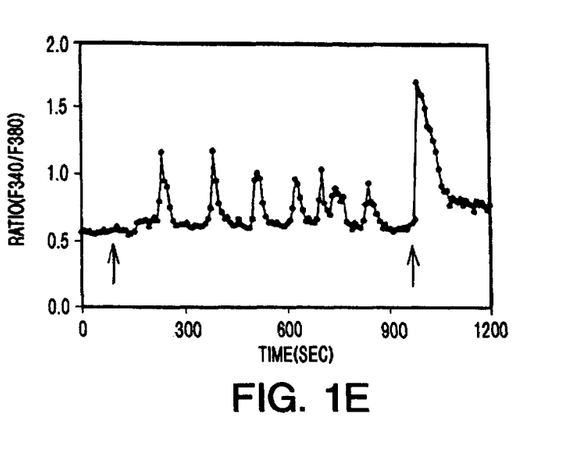
Figure 1F:
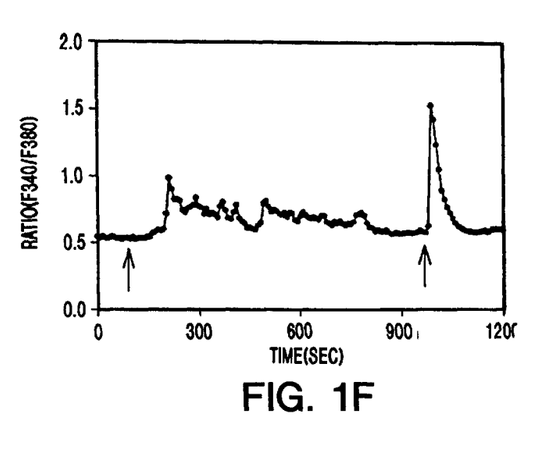
FIG. 1F shows a cell responding with a combination of a prolonged plateau and oscillations. Finally.
Figure 1G:
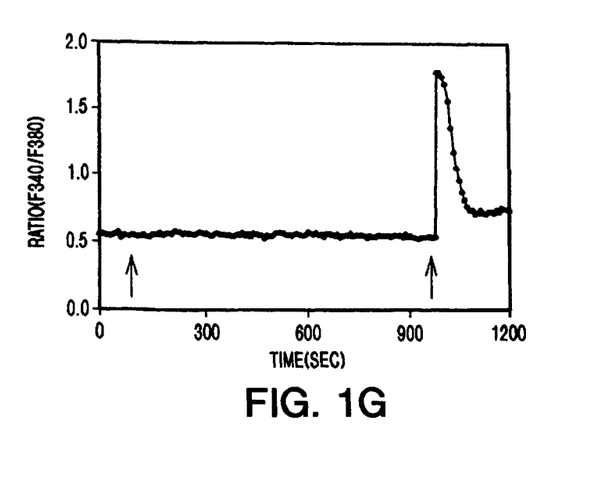
FIG. 1G and FIG. 1H show cells that do not respond to bFGF stimulation. All cells respond rapidly and synchronously with a sharp calcium spike to 10 $\mu$M bradykinin (second arrow) which serves as a positive control for both responsiveness and cell viability.
Figure 1H:
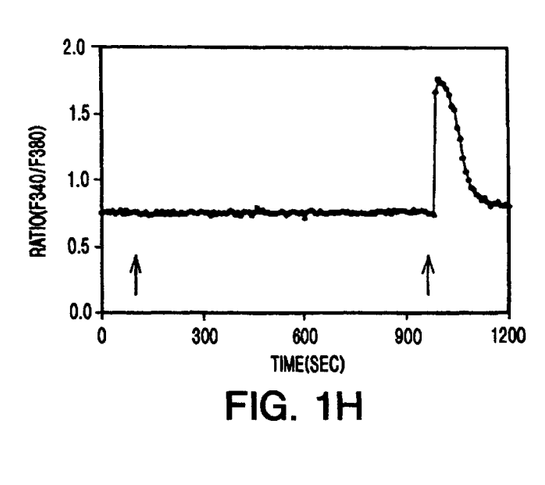

Cells have a robust response to growth factors when serum deprived, either because they are all in $G_0$ or because the receptors have been upregulated in the absence of ligand. Standard conditions were chosen as the response of serum deprived human diploid fibroblasts to the addition of 50 ng/ml bFGF in Ringer solution, a supra maximal dose for triggering intracellular calcium waves. As illustrated in FIG. 1, during the first minute of baseline, agonist free measurement, cells have a stable resting cytosolic ionized free calcium concentration of between 100 and 200 nM. Upon the addition of bFGF (indicated by the first arrow in the figure), but after a variable time lag ranging from 15 seconds (the time required for a fivefold volume exchange of the bath perfusion system) to 180 seconds, individual cells respond asynchronously with calcium wave signals. This asynchronous response, with each cell's calcium oscillating out of phase with that of its neighbors, makes these signals very difficult to resolve without sophisticated single-cell analysis. In addition, the individual signals varied in the nature of the calcium wave which developed. These were broadly characterized as single transients, sustained plateaus, or oscillations in the intracellular calcium concentration. The transients (FIG. 1D) typically have a duration of 1–2 min. They are indistinguishable from the first calcium wave seen in cells that go on to oscillate (FIGS. 1A, B, and E), and may, therefore, reflect a special case of the same response. Should oscillations ensue, the calcium waves occur at regular intervals, 2–3 min between peaks, and the amplitude of the waves diminishes with time. The sustained plateau response (FIG. 1C) appears distinctly different, and may, if fact, be superimposed upon the oscillations (FIG. 1F). It may be slow to rise, but has as its distinctive feature a sustained, still slower, declining phase back to baseline. At the end of each experiment bradykinin (10 $\mu$M) was added to the cells. Bradykinin is known to act through its own G protein coupled serpentine receptor and to mediate phosphoinositol turnover and IP3-dependent calcium release from intracellular stores (Etscheid, B., et al., 1989, J. Cell. Physiol. 140:264–271). The bradykinin response, therefore, served as a positive control in each experimental cell for both viability and a responsive calcium signaling pathway. It, further, served as a check on the calibration of the imaging apparatus itself. Note that not every cell responded to bFGF (FIGS. 1G and H), even though its bradykinin response was intact.

Previous studies have shown that growth factors such as platelet derived growth factor (PDGF), epidermal growth factor (EGF) and FGF, in binding to their receptor tyrosine kineses, mediate cytoplasmic calcium waves produced by a combination of calcium release from intracellular stores, and a sustained calcium current across the plasma membrane. In most cases the conductance pathway can be defined as either a voltage-activated calcium channel (e.g., Curran, T., and Morgan, J., 1986, Proc. Natl. Acad. Sci. U.S.A. 83:8521–8524), a nonselective cation channel (e.g., Peppelenbosch, M. P., et al., 1992, Cell 69:295–303) or a calcium conductance that appears to open as a consequence of the emptying of the internal calcium stores, called the calcium release activated current, or Icrac (e.g., Putney, J. W., and Bird, G. S., 1993, Cell 75:199–201).

Figure 2A:
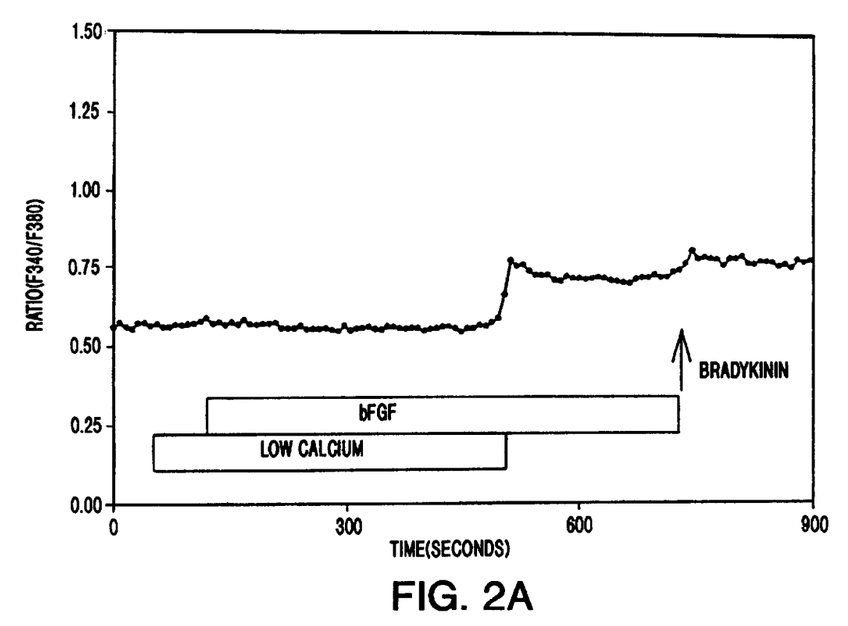
FIG. 2A shows dye added in nominally calcium-free (~1 $\mu$M) buffer. Under these conditions, 50 ng/ml bFGF is unable to elicit a calcium signal until after the extracellular calcium concentration has been restored to the physiological level of 2 mM.
Figure 2B:
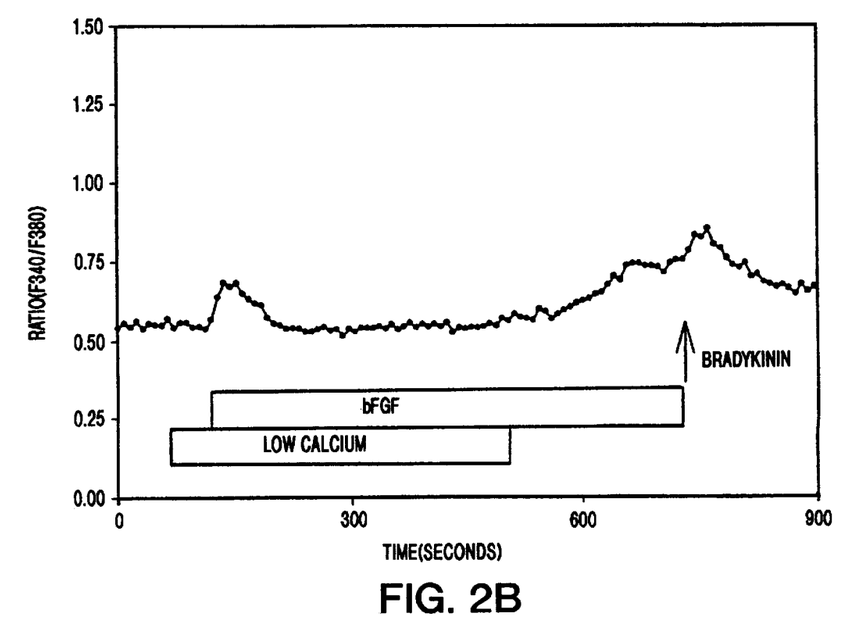
FIG. 2B shows an occasional, small brief transient calcium signal which is elicited in the nominally calcium-free buffer upon bFGF addition, which, after the restoration of physiological external calcium becomes a sustained plateau.

This later paradigm was analyzed in wild-type human fibroblasts to define the mechanism underlying the calcium oscillatory waves. By comparing the response to bFGF in nominally calcium free (~1 $\mu$M) Ringer solution with the response at normal extracellular calcium, a role for calcium release could be tested. FIG. 2 shows that bFGF fails to cause calcium signals in the absence of extracellular calcium. The implication is that the bFGF-induced calcium signal in human diploid fibroblasts is primarily dependent upon extracellular calcium entering the cytoplasm, with no significant component produced by the release of intracellular calcium stores. Since, after the readdition of external calcium, the cells could resume their responses, similar to those shown in FIG. 1, transmembrane calcium influx must be predominantly responsible for the FGFR calcium signal. These results in human cells are consistent with results in the murine Balb-c 3T3 fibroblast line (Munaron, L., et al., 1995, J. Physiol. 484:557–566), who found that bFGF elicited a sustained increase in intracellular calcium and that this was completely dependent upon external calcium and the continued presence of the mitogen. The sustained increase in intracellular calcium did not depend upon internal store depletion since the addition of thapsigargin, an inhibitor of the ion pump which keeps the $IP_3$-sensitive and -insensitive $Ca^{2+}$ stores filled (Lytton, J., et al., 1991, J. Biol. Chem. 226:17067–17071), did not elicit any inward current in those cells. This same pharmacology appears to be present in the human fibroblasts. The bFGF induced calcium signal in human diploid fibroblasts, therefore, seems to be produced by a transmembrane calcium influx though an as yet undefined calcium-conducting channel.

EXAMPLE 3

Effect of FGFR3 Mutations on the Calcium Signal

Figure 3A:
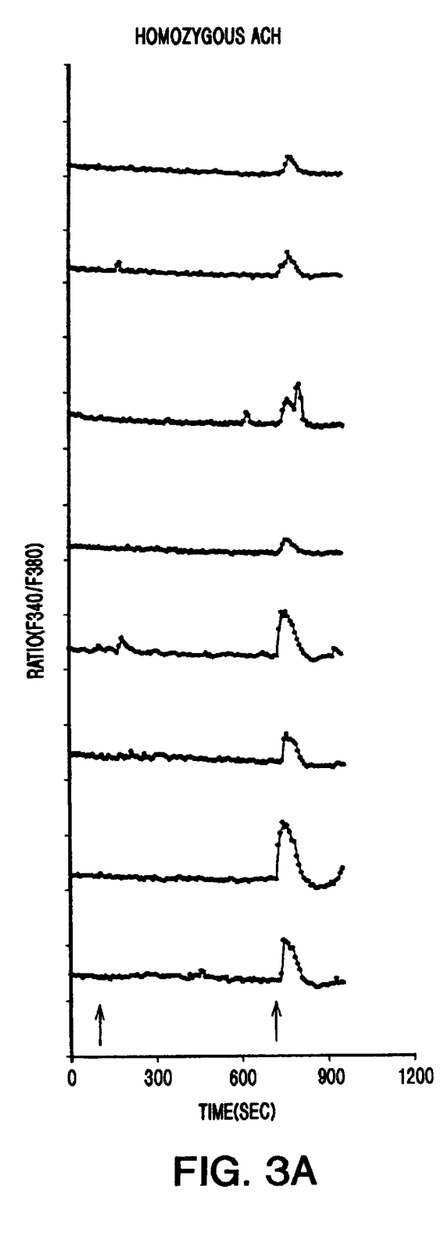
Figure 3B:
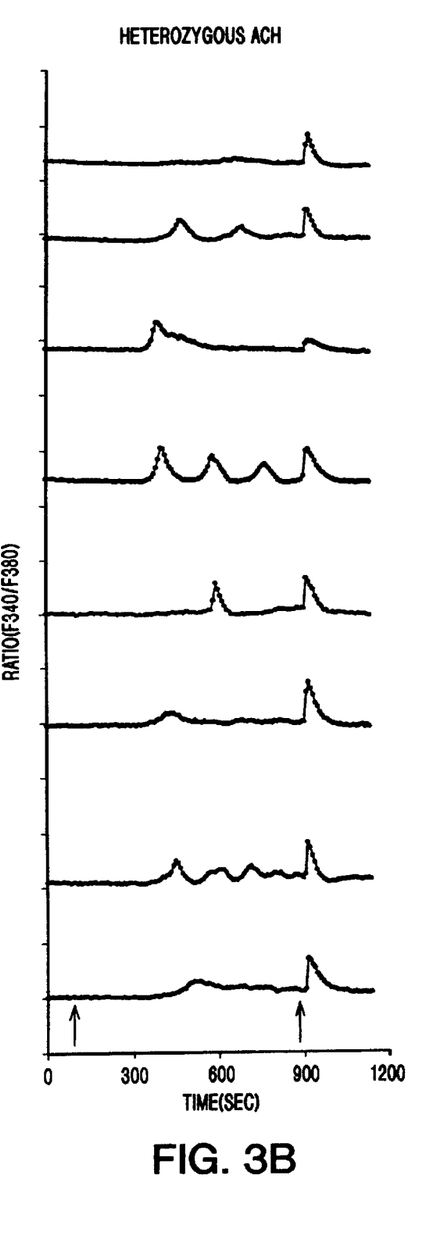
Figure 3C:
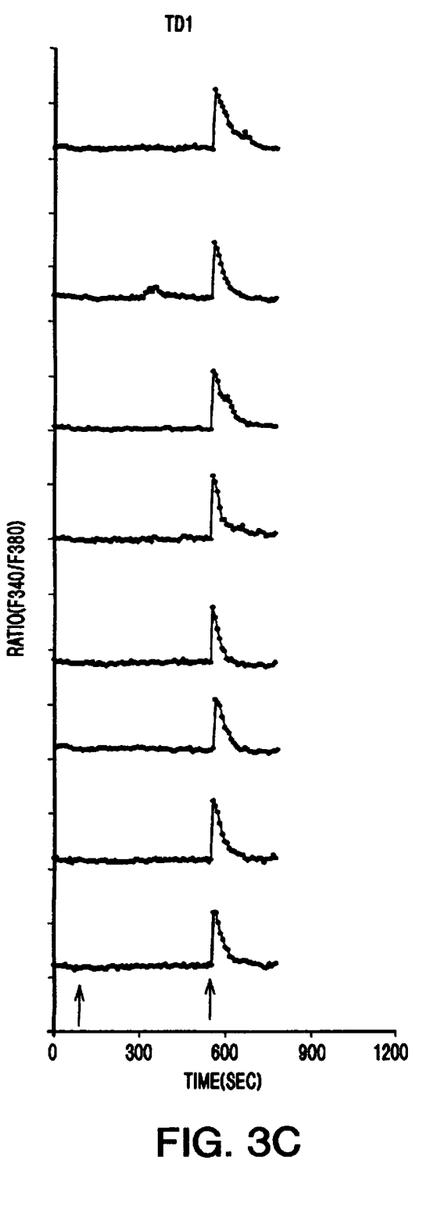
Figure 3D:
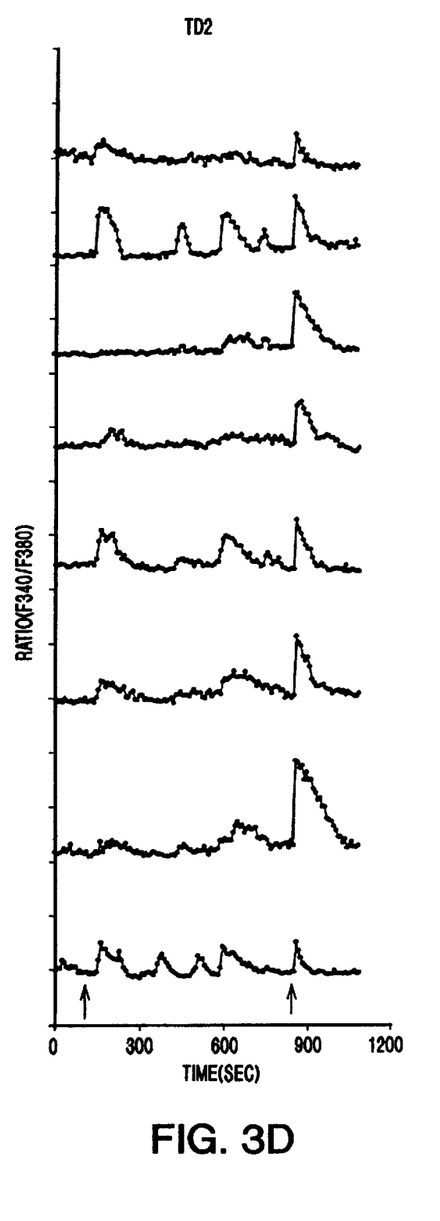

To further define the mechanism of bFGF induced calcium signals in human diploid fibroblasts, and in particular to assess the effect of FGFR3 on calcium signals, the bFGF response of cells with defined mutations in FGFR3 was examined. The cells studied, in addition to wild-type, carried defined mutant alleles which produced the distinctive disease phenotypes of homozygous and heterozygous achondroplasia and types 1 and 2 thanatophoric dysplasia (Shiang, R., et al., 1994, Cell 78:1–20; Tavormina, P. L., et al., 1995, Nature Genet. 9:321–328). FIG. 3 presents the analysis of 8 representative cells having genotypes causing each of these four disease phenotypes. The studies are carried out in normal extracellular calcium, and are directly comparable to the study of wild-type control cells presented in FIG. 1. FIGS. 3A and 3B show that calcium signaling by fibroblasts in response to bFGF is altered by mutations in FGFR3. FIGS. 3A, 3B, 3C, and 3D each show eight representative cells from genotyped individuals having homozygous achondroplasia, heterozygous achondroplasia, heterozygous TD1 thanatophoric dysplasia, or heterozygous TD2 thanatophoric dysplasia, respectively. To allow for a condensed presentation, the tracings are offset vertically from each other and the Y-axis tick-marks represent 0.5 fluorescence ratio units. A homozygous G380R mutation in FGFR3 eliminates calcium signaling by all FGF receptors and effectively abolishes the composite response to bFGF (FIG. 3A); however, the heterozygous G380R genotype gives a normal calcium signal (FIG. 3B). A single TD1 mutant allele of FGFR3 results in the complete inhibition of all bFGF-dependent calcium signaling (FIG. 3C), whereas a single K650E TD2 allele of FGFR3 does not alter calcium signaling (FIG. 3D). Note that none of the above mutations has any effect on the baseline calcium or on the ability of bradykinin to elicit a control calcium signal. Statistical analysis of the prestimulation ratio values by ANOVA showed no significant differences between any groups or between any group and wild-type.

These results show that the baseline calcium concentration is indistinguishable for all four disease phenotypes, and that it is the same as found in wild-type control cells, approximately 100 to 200 nM. Furthermore, none of the cells show a constitutive signaling phenotype. None of these serum-deprived mutant cells shows constitutive calcium waves or even an elevated cytosolic calcium concentration, as would be expected if their FGFRs were constitutively active in the absence of ligand.

The addition of bFGF induces calcium signals in cells with genotypes causing heterozygous achondroplasia and heterozygous type 2 thanatophoric dysplasia. These signals are comparable to those of wild-type cells in morphology and duration. On the other hand, the calcium signal is largely obliterated in cells with genotypes causing heterozygous type 1 thanatophoric dysplasia and homozygous achondroplasia. Only occasionally did a cell in these fields give even an aberrant calcium signal in response to bFGF, despite the fact that they signaled perfectly normally in response to bradykinin. For all four mutant cell types, the bradykinin response appears in every way to be the same as in wild-type control cells. This is a further reassurance that the mutant cells do not have a constitutive calcium signaling phenotype. Since image analysis allows us to follow only net changes in cytosolic calcium, one might imagine the mutant cells masking an increased constitutive unidirectional calcium influx by somehow having increased unidirectional efflux. This cannot be the case, however, since this increased unidirectional efflux would have had to alter the kinetics of the bradykinin induced calcium signal as well, contrary to what was observed.

Figure 4:
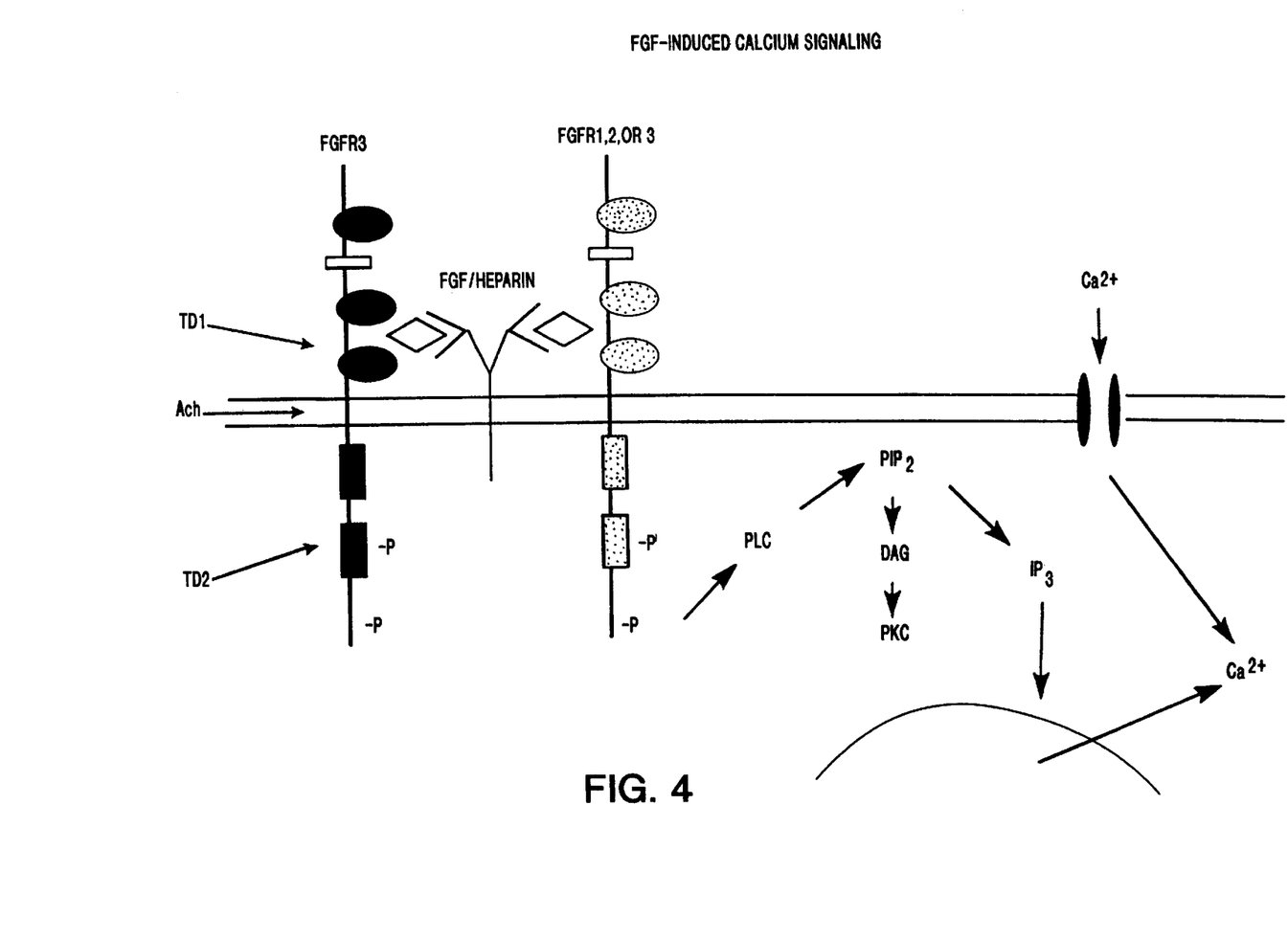

To determine the reliability of the phenotypes ascertained by calcium image analysis, multiple independent cell lines having different FGFR3 alleles were examined in a single-blinded fashion for response to bFGF. Table IV presents the response rate determined on ~250 cells of each cell line, and FIG. 4 illustrates FGFR calcium signaling and the position of the different FGFR3 mutations studied. FIG. 4 shows a model for FGF receptor signaling. FGF binds to heparin and produces hetero- and homo-multimers of the FGFRs, activating their endogenous tyrosine kinase. Within this complex the receptors undergo autophosphorylation on tyrosine residues. PLC$\gamma$ docks on phosphotyrosine 766, becomes phosphorylated and active, cleaving phosphatidylinositol 4,5-bisphosphate (PIP2) to diacylglycerol (DAG) and inositol 1,4,5-triphosphate (IP3). DAG activates Protein kinase C (PKC) and IP3 releases calcium from intracellular stores by binding to an IP3 receptor. The mechanism by which the calcium conducting ion channel in the plasma membrane becomes activated remains to be determined, but the majority are not Icrac channels.

Figure 5:
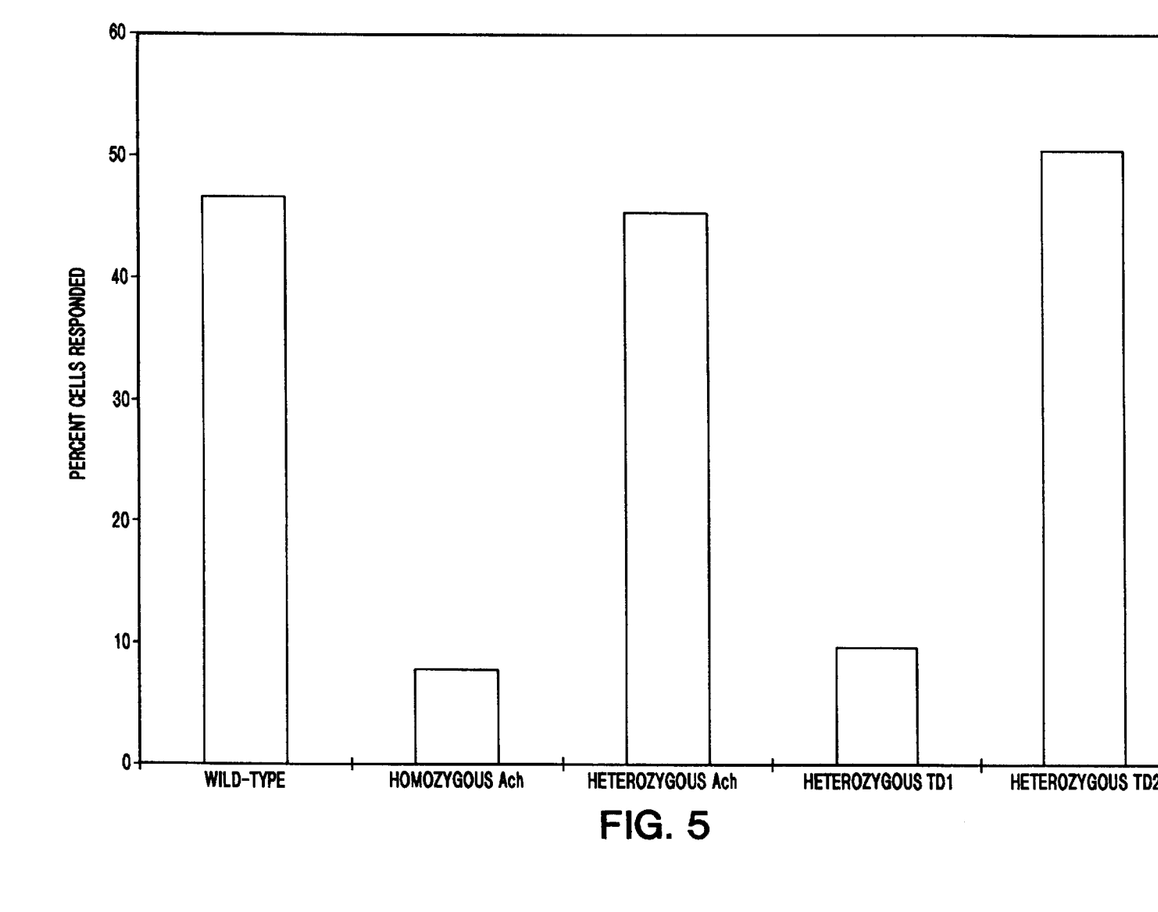
FIG. 5 shows mean response rates of cells with different FGFR3 genotypes. This bar graph illustrates the mean response rate of each group of cell lines presented in Table 1. 47±19 percent of wild-type cells responded. This compares with 45±21 percent of heterozygous achondroplasia cells and 50±25 percent of heterozygous TD2 cells, and contrasts with the low response rates of homozygous achondroplasia and heterozygous TD1 cells, having only 8±8 and 10±4 percent responses, respectively.

In Table IV, the percent of cells responding to bFGF with any form of calcium signal is reported and all cells carrying a genotype causing a given disease phenotype are grouped. Note the internal consistency within groups. Cells subsequently revealed to have been genotyped as homozygous Ach or heterozygous TD1 had fewer than 10% of the population respond to bFGF, and no individual line had greater than one out of six cells capable of any type of bFGF response. All of the other genotypes responded similarly to control at ~45%. This is graphically represented in FIG. 5 as the mean response rate for cells from each of the disease groups. FIG. 5 shows mean response rates of cells with different FGFR3 genotypes. This bar graph illustrates the mean response rate of each group of cell lines presented in Table 1. 47±19 percent of wild-type cells responded. This compares with 45±21 percent of heterozygous achondroplasia cells and 50±25 percent of heterozygous TD2 cells, and contrasts with the low response rates of homozygous achondroplasia and heterozygous TD1 cells, having only 8±8 and 10±4 percent responses, respectively.

As was observed when comparing the morphology of calcium signals produced by cells of different genotypes, the high response rates in heterozygous achondroplasia and heterozygous type 2 thanatophoric dysplasia are comparable to that of wild-type, whereas the heterozygous type 1 thanatophoric dysplasia and homozygous achondroplasia cells rarely responded to bFGF.

TABLE IV

Calcium Response Rates in Individual Cell Lines

| Cell Line | % Responding |
|---|---|
| Control | |
| WT1 | 27 |
| WT2 | 66 |
| WT3 | 47 |
| Homozygous Ach | |
| HAch 1 | 0 |
| Hach2 | 6 |
| Hach3 | 16 |
| Heterozygous Ach | |
| Ach 1 | 53 |
| Ach2 | 14 |
| Ach3 | 54 |
| Ach4 | 60 |
| TD1 | |
| TD11 | 8 |
| TD12 | 12 |
| TD13 | 13 |
| TD14 | 5 |
| TD2 | |
| TD21 | 88 |
| TD22 | 46 |
| TD23 | 38 |
| TD24 | 31 |

In more detail, Table IV shows the response rate of individual cell lines to 50 ng/ml bFGF. Approximately 250 cells from each cell line were analyzed for changes in intracellular calcium using ratiometric image analysis, as described in Example 1. A cell was considered responsive if bFGF elicited a calcium signal like any of those in FIGS. 1A–F. Only cells responding to bradykinin were scored.

These experiments show that in human diploid fibroblasts, as in previously studied model systems, calcium signaling is a useful downstream reporter of physiological FGF receptor activation, and demonstrate that in the fibroblasts this signal is predominated by a transmembrane calcium influx. The work further shows that this physiological reporter function can be used to assign a signaling phenotype to single cells, and that this single-cell phenotype is highly correlated with certain FGFR3 disease phenotypes.

Without wishing to be bound by theory, it is believed that the mutant FGFR3 alleles function to disrupt signaling in a dominant negative manner. The results are inconsistent with a constitutive functional activation of signaling by the mutant receptors since the mutant and wild-type cells have the same stable, low basal intracellular calcium concentration during serum starvation, and achieve comparable calcium waves of comparable magnitude and duration during control bradykinin or ATP activations. This is also consistent with the well established observation that these alleles lack any oncogenic potential in vivo or in vitro. A dominant negative interaction, on the other hand, is implied since cells of specific FGFR3 genotypes faithfully remain at basal calcium concentrations after supra maximal bFGF stimulation, a result that could not be achieved without the mutant allele acting through some novel gained function to silence all responses to bFGF.

The results show that a single copy of either ligand binding domain TD1 allele tested (R248C or S371C), or homozygosity for the common transmembrane domain achondroplasia allele (G380R), inhibit all $Ca^{2+}$ signaling induced by bFGF, a faithful and predictive, possibly diagnostic, correlate of their characteristic lethal phenotypes. The fact that all bFGF-dependent $Ca^{2+}$ signaling was abolished by these genotypes at the FGFR3 locus suggests that the abnormal FGFR3 in some way interferes with signaling by the other expressed allelic and nonallelic wild-type FGF receptors.

In the homozygous state, the absence of any wild-type FGFR3, and the expression of two copies of the inhibitory mutant FGFR3 allele, against a background of wild-type FGFR1 and FGFR2 expression, produces a mix of FGF receptors unable to produce a threshold physiological response to even supra maximal bFGF. In heterozygous achondroplasia, the expression of less mutant and more wild-type FGFR3, with no change in the other members of this receptor family, yields a receptor mix still capable of producing the threshold downstream signal that allows physiological calcium signaling to occur.

The results also suggest that a critical aggregate level of receptor activity must be induced by ligand binding to cross a threshold, which allows physiological calcium signaling to occur. Just as two, but not one, copies of the G380R allele leave receptor activity below threshold, even one copy of any of the TD1 alleles prevents calcium signaling. Therefore the TD1 alleles must be more disruptive dominant negative alleles than the G380R allele. This increased potency might arise because of increased avidity in interactions with other receptor monomers, or it might arise by interference at a different, more sensitive step in the signaling. One copy of the TD2 kinase domain allele, K650E, is not sufficient to suppress calcium signaling. The implication is that the TD2 allele is less disruptive or potent than the TD1 alleles, again either because of a lesser avidity at the same site acted upon by TD1 or because it acts at a less sensitive step in the signaling. Because the disease phenotype produced by a single TD2 allele is much more severe than that produced by a single G380R achondroplasia allele, the TD2 allele must be more disruptive than a single G380R allele. This would give an overall negative dominant allele potency of TD1>TD2>Ach.

Because an equivalently severe perinatal-lethal disease phenotype produced by homozygous achondroplasia, and heterozygous TD1 and TD2 thanatophoric dysplasia, the dominant negative hypothesis suggests that the disruptive potency of the homozygous G380R genotype is severe, but incompletely determined, being either more severe than both TD1 and TD2 or intermediate between the two. This would order the disruptive potency of the genotypes as (HAch~TD1)>fibroblast threshold>TD2>Ach. That the tissue most critical to the pathogenesis of the syndromes (perhaps the embryonic endochondral growth plate chondrocytes) must be more sensitive to FGF signaling than the fibroblast model cells (i.e., signaling threshold must be higher) is also suggested by these results. Thus, even a single achondroplasia allele has some effect, giving an order: (HAch~TD1)>fibroblast threshold>TD2>key threshold>Ach>WT.

Although the invention has been described with reference to the presently preferred embodiment, it should be understood that various modifications can be made without departing from the spirit of the invention. Accordingly, the invention is limited only by the following claims.

What is claimed is:

1. A method of detecting a congenital disorder in a subject having an altered membrane component comprising:
    a) contacting a sample of fetal cells obtained from the subject with a substance normally able to activate the membrane component in a wild type cell; and
    b) detecting an intracellular second messenger response after said contacting, wherein an abnormal second messenger response is indicative of a congenital disorder in the subject.

2. The method of claim 1, further comprising:
    comparing said second messenger response in said sample of fetal cells to the second messenger response in a sample of wild type cells having a normal second messenger response to activation of the membrane component.

3. The method of claim 1, wherein said second messenger response is an ion flux.

4. The method of claim 3, wherein said ion flux is a calcium flux.

5. The method of claim 1, wherein said membrane component is a receptor.

6. The method of claim 5, wherein said receptor is a fibroblast growth factor receptor.

7. The method of claim 6, wherein said congenital disorder is associated with a mutation in a nucleic acid encoding a fibroblast growth factor receptor.

8. The method of claim 1, wherein said congenital disorder is selected from the group consisting of achondroplasia; thanatophoric dysplasia type 1; thanatophoric dysplasia type 2; Crouzon, Jackson-Weiss, Pfeiffer and Apert syndrome; hypochondroplasia; Crouzon syndrome with acanthosis nigricans; and fibroblast growth factor receptor 3-associated coronal synostosis.

9. The method of claim 1, wherein a physiological indicator probe is used to determine said second messenger response.

10. The method of claim 9, wherein said physiological indicator probe is a calcium indicator dye.

11. The method of claim 1, wherein the sample of fetal cells is obtained by amniocentesis, chorionic villus sampling, percutaneous umbilical cord sampling or fetal biopsy.

12. A method of detecting a bone development disorder associated with a mutation in a fibroblast growth factor receptor in a subject having an altered membrane component comprising:
    a) contacting a sample of cells obtained from the subject with a substance normally able to activate the membrane component in a wild type cell; and
    b) detecting an intracellular second messenger response after said contacting, wherein an abnormal second messenger response is indicative of the bone development disorder in the subject.

13. The method of claim 12, further comprising:
    comparing said second messenger response in said sample of cells to the second messenger response in a sample of wild type cells having a normal second messenger response to activation of the membrane component.

14. The method of claim 12, wherein said bone development disorder is selected from the group consisting of achondroplasia; thanatophoric dysplasia type 1; thanatophoric dysplasia type 2; Crouzon, Jackson-Weiss, Pfeiffer and Apert syndrome; hypochondroplasia; Crouzon syndrome with acanthosis nigricans; and fibroblast growth factor receptor 3-associated coronal synostosis.

15. The method of claim 12, wherein said second messenger response is an ion flux.

16. The method of claim 15, wherein said ion flux is a calcium flux.

17. The method of claim 12, wherein a physiological indicator is used to determine said second messenger response.

18. The method of claim 17, wherein said physiological indicator is a calcium indicator dye.

19. The method of claim 12, wherein said sample of cells is a skin biopsy or a blood sample.

20. A method for determining that a disorder in a subject is associated with a mutation of a fibroblast growth factor receptor (FGFR) in a cell, comprising the steps of:
    a) contacting a cell obtained from the subject with a substance that activates an FGFR in a wild type cell; and
    b) detecting an intracellular second messenger response after said contacting, wherein an abnormal second messenger response indicates that the disorder in the subject is associated with a mutation in an FGFR in the cell.

21. The method of claim 20, wherein said second messenger response is an ion flux.

22. The method of claim 21, wherein said ion flux is a calcium flux.

23. The method of claim 21, wherein a physiological indicator probe is used to determine said ion flux.

24. The method of claim 23, wherein said physiological indicator probe is a calcium indicator dye.

25. The method of claim 20, wherein the cell obtained from the subject is a prenatal cell.

26. A method of detecting a congenital disorder in a subject, comprising:
    a) introducing a physiological indicator into prenatal cells obtained from the subject;
    b) contacting said cells with a ligand that can activate a receptor expressed in a wild type cell;
    c) detecting the effect of said ligand on said physiological indicator in the prenatal cells obtained from the subject; and
    d) comparing said effect of the ligand on said physiological indicator with the effect of the ligand on said physiological indicator in the wild-type cell, wherein a difference in effect is indicative of a congenital disorder in a subject.

27. The method of claim 26, wherein said ligand binds a cell membrane receptor.

28. The method of claim 27, wherein said cell membrane receptor is a fibroblast growth factor receptor.

29. The method of claim 27, wherein said ligand binding of said cell membrane receptor normally regulates a cell signaling pathway that affects said physiological indicator.

30. The method of claim 26, wherein said physiological indicator is a calcium indicator dye.

31. The method of claim 26, wherein said congenital disorder is associated with a mutation in a fibroblast growth factor receptor.

32. The method of claim 26, wherein said congenital disorder is selected from the group consisting of achondroplasia; thanatophoric dysplasia type 1: thanatophoric dysplasia type 2; Crouzon, Jackson-Weiss, Pfeiffer and Apert syndrome; hypochondroplasia; Crouzon syndrome with acanthosis nigricans; and fibroblast growth factor receptor 3-associated coronal synostosis.

* * * * *